US 011471143B2

(12) United States Patent
Kondapalli

(10) Patent No.: US 11,471,143 B2
(45) Date of Patent: Oct. 18, 2022

(54) EYELID RETRACTOR AND IRRIGATION TOOL

(71) Applicant: Srinivas Sai Appala Kondapalli, Gibsonia, PA (US)

(72) Inventor: Srinivas Sai Appala Kondapalli, Gibsonia, PA (US)

(*) Notice: Subject to any disclaimer, the term of this patent is extended or adjusted under 35 U.S.C. 154(b) by 349 days.

(21) Appl. No.: 16/783,850

(22) Filed: Feb. 6, 2020

(65) Prior Publication Data

US 2020/0275918 A1    Sep. 3, 2020

Related U.S. Application Data

(60) Provisional application No. 62/802,176, filed on Feb. 6, 2019.

(51) Int. Cl.
*A61B 17/02* (2006.01)
*A61M 3/02* (2006.01)

(52) U.S. Cl.
CPC ....... *A61B 17/0231* (2013.01); *A61M 3/0254* (2013.01); *A61M 3/0279* (2013.01); *A61B 2217/007* (2013.01)

(58) Field of Classification Search
CPC ......... A61B 17/0231; A61B 2217/007; A61M 3/0254; A61M 3/0262; A61M 3/0279; A61M 3/0283; A61M 2210/0612
USPC ....................................... 600/205, 210, 236
See application file for complete search history.

(56) References Cited

U.S. PATENT DOCUMENTS

| | | | |
|---|---|---|---|
| 4,834,727 A * | 5/1989 | Cope | A61B 17/0231 604/300 |
| 5,084,012 A * | 1/1992 | Kelman | A61M 1/85 604/35 |
| 5,387,201 A * | 2/1995 | Fowler | A61M 3/0279 604/290 |
| 5,762,606 A | 6/1998 | Minnich | |
| 5,795,342 A | 8/1998 | Shapiro et al. | |
| 5,800,406 A * | 9/1998 | Kritzinger | A61F 9/0133 604/35 |
| 6,346,078 B1 * | 2/2002 | Ellman | A61B 17/0231 600/235 |
| 6,423,074 B1 * | 7/2002 | Chen | A61F 9/00736 606/107 |
| 7,175,594 B2 | 2/2007 | Foulkes | |

(Continued)

FOREIGN PATENT DOCUMENTS

WO    2011162360 A1    12/2011

*Primary Examiner* — Eduardo C Robert
*Assistant Examiner* — David C Comstock
(74) *Attorney, Agent, or Firm* — The Webb Law Firm

(57) ABSTRACT

An eyelid retractor and irrigation tool includes a handle portion defining a longitudinal first axis configured to be grasped by a user and a hook portion connected to the handle portion for retracting an eyelid. The hook portion of the tool includes: inwardly and outwardly facing walls, which are curved about a second axis, which is distinct from the first axis; an edge wall extending between the inwardly and outwardly facing walls; and an interior cavity defined by the walls. The tool further comprises at least one opening extending through the inwardly facing wall or the outwardly facing wall fluidly connected to the interior cavity and positioned such that fluid in the interior cavity passes through the at least one opening to irrigate portions of an eye including the eyelid.

22 Claims, 14 Drawing Sheets

(56) References Cited

U.S. PATENT DOCUMENTS

| | | |
|---|---|---|
| 8,915,848 B1 | 12/2014 | Rixen |
| 11,266,776 B2* | 3/2022 | Wen ............... A61M 5/3137 |
| 2003/0171656 A1* | 9/2003 | Foulkes ........... A61B 1/00094 |
| | | 600/232 |
| 2007/0179457 A1 | 8/2007 | Whitmore et al. |
| 2012/0136322 A1* | 5/2012 | Alster ............. A61K 31/5575 |
| | | 604/290 |
| 2015/0257928 A1* | 9/2015 | Iseli ............... A61F 9/0017 |
| | | 604/93.01 |
| 2016/0287438 A1* | 10/2016 | Badawi ............ A61K 31/728 |
| 2019/0192342 A1 | 6/2019 | Maloney et al. |

* cited by examiner

EYELID RETRACTOR AND IRRIGATION TOOL

CROSS REFERENCE TO RELATED APPLICATION

The present application claims the benefit of U.S. Provisional Patent Application Ser. No. 62/802,176, filed Feb. 6, 2019, the entire disclosure of which is hereby incorporated by reference.

BACKGROUND OF THE INVENTION

Field of the Invention

This disclosure is directed to a tool for irrigation and cleaning of portions of the eye and, in particular, to a tool configured to provide liquid and/or gas to portions of the eyelid, conjunctiva, and/or eyeball, for removing foreign material, irritants, and debris.

Description of Related Art

It is often necessary to clean or flush debris and foreign material from the eye, eyeball, and/or eyelid following a medical procedure. For example, cleaning agents or antiseptics, such as Betadine (povidone-iodine), may be introduced to the eye during a medical procedure. Other agents, such as dyes, therapeutic agents, and similar compositions, may also be provided to the eye during the procedure. In some cases, these chemical agents should be flushed from the eye following the procedure to avoid irritating the eye.

Conventionally, in order to clean or flush the eye, the practitioner or the patient will use his or her fingers to push the eyelid away from the eye and then dispense a cleaning solution, such as saline solution, using, for example, an eyedropper or container with a liquid-dispensing nozzle. Eyelid retracting tools for moving the eyelid away from the eye so that more dispensed liquid contacts the eye are known. Such tools can be helpful for improving access to the eye to assist in removing debris and foreign material from portions of the eye. One tool, known as a Desmarres retractor, includes a curved blade configured to grasp and pull the eyelid away from the eye. Tools including other arrangements of blades or protrusions for grasping the eyelid are also known, as described, for example, in U.S. Pat. No. 8,915,848.

Devices that retract the eyelid and dispense liquid towards the eye are also known. For example, U.S. Pat. Nos. 5,762,606 and 5,795,342, disclose devices that retract both the upper and lower eyelids to improve access to the eye. These devices also include fluid dispensing mechanisms for providing liquid towards the cornea of the eye to clean the eye or to introduce other types of medical solutions to the eye.

SUMMARY OF THE INVENTION

In one non-limiting embodiment, an eyelid retractor and irrigation tool includes a handle portion defining a longitudinal first axis configured to be grasped by a user and a hook portion for retracting an eyelid connected to the handle portion. The hook portion includes: inwardly and outwardly facing walls, which are curved about a second axis, which is distinct from the first axis; an edge wall extending between the inwardly and outwardly facing walls; and an interior cavity defined between the walls. The tool further includes at least one opening extending through the inwardly facing wall or the outwardly facing wall fluidly connected to the interior cavity and positioned such that fluid in the interior cavity passes through the at least one opening to irrigate portions of an eye including the eyelid.

Examples of the present invention will now be described in the following numbered clauses:

Clause 1: An eyelid retractor and irrigation tool, comprising: a handle portion defining a longitudinal first axis configured to be grasped by a user; a hook portion for retracting an eyelid connected to the handle portion, the hook portion comprising: inwardly and outwardly facing walls, which are curved about a second axis, which is distinct from the first axis; an edge wall extending between the inwardly and outwardly facing walls; and an interior cavity defined between the walls; and at least one opening extending through the inwardly facing wall or the outwardly facing wall fluidly connected to the interior cavity and positioned such that fluid in the interior cavity passes through the at least one opening to irrigate portions of an eye including the eyelid.

Clause 2: The tool of clause 1, wherein the first axis is spaced apart from the second axis along an entire length of the axes.

Clause 3: The tool of clause 1 or clause 2, wherein a surface of the outwardly facing wall generally conform to a shape of an eyeball.

Clause 4: The tool of any of clauses 1-3, wherein the handle portion comprises a fluid channel in fluid communication with the interior cavity of the hook portion.

Clause 5: The tool of any of clauses 1-3, wherein the handle portion comprises an elongated member comprising a fluid channel extending through at least a portion of the handle portion in fluid communication with the interior cavity of the hook portion.

Clause 6: The tool of clause 5, wherein at least a portion of the handle portion has a polygonal cross section, and wherein at least a portion of the fluid channel through the polygonal cross section has a circular cross section.

Clause 7: The tool of clause 5 or clause 6, wherein the fluid channel comprises a first end at a proximal end of the elongated member and a second end, opposite the first end, which is connected to the interior cavity of the hook portion.

Clause 8: The tool of any of clauses 5-7, further comprising a liquid container mounted to the handle portion, wherein the container comprises an interior in fluid communication with the fluid channel for introducing liquid into the fluid channel to be expelled from the at least one opening extending through the inwardly facing wall or the outwardly facing wall.

Clause 9: The tool of clause 8, wherein the handle portion comprises at least one opening extending through a sidewall of the elongated member, and wherein the liquid container comprises an open end connected to the at least one opening of the handle portion, such that liquid from the liquid container is provided into the fluid channel through the at least one opening of the handle portion.

Clause 10: The tool of clause 8 or clause 9, further comprising a compressible bulb mounted to the handle portion comprising an interior in fluid communication with the fluid channel, wherein compressing the bulb pushes gas into the fluid channel to expel liquid from the liquid container through the fluid channel to the interior cavity of the hook portion and through the at least one opening of the hook portion.

Clause 11: The tool of any of clauses 5-7, further comprising: a first liquid container mounted to the handle portion comprising an interior in fluid communication with the fluid channel for introducing a first liquid into the fluid channel through at least one first opening in a sidewall of the elongated member; a second liquid container mounted to the handle portion comprising an interior in fluid communication with the fluid channel for introducing a second liquid into the fluid channel through at least one second opening in the sidewall of the elongated member; and a compressible bulb mounted to the handle portion comprising an interior in fluid communication with the fluid channel, wherein compressing the bulb pushes gas into the fluid channel to expel the first liquid and the second liquid from the fluid channel to the interior cavity of the hook portion and through the at least one opening of the hook portion.

Clause 12: The tool of clause 11, wherein the compressible bulb is mounted to a proximal end of the elongated member and introduces the gas into the fluid channel through a proximal end of the fluid channel.

Clause 13: The tool of any of clauses 1-12, further comprising an intermediate portion between the handle portion and the hook portion, wherein the intermediate portion is tapered such that a width of the hook portion is greater than a width of the handle portion.

Clause 14: The tool of any of clauses 1-13, wherein the hook portion comprises an arcuate profile with a radius of from 5 mm to 10 mm.

Clause 15: The tool of any of clauses 1-14, wherein the hook portion comprises at least one opening extending from the interior cavity through the outwardly facing wall, and at least one opening extending from the cavity through the inwardly facing wall.

Clause 16: The tool of clause 15, wherein the hook portion further comprises at least one opening extending from the interior cavity through the edge wall.

Clause 17: The tool of any of clauses 1-14, wherein the hook portion comprises a plurality of openings extending through the outwardly facing wall and a plurality of openings extending through the inwardly facing wall, and wherein the pluralities of openings are arranged in at least two rows extending substantially parallel to the second axis.

Clause 18: The tool of any of clauses 1-17, further comprising a fluid bottle and a tube extending therefrom, wherein the tube is connected to a fluid channel extending through the handle portion and the hook portion to the interior cavity.

Clause 19: The tool of clause 18, wherein fluid expelled from the fluid bottle passes through the tube and the fluid channel to the interior cavity of the hook portion.

Clause 20: The tool of clause 19, further comprising a valve in fluid communication with the bottle and the tube for controlling distribution of the fluid from the fluid bottle.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. As used in the specification and the claims, the singular form of "a", "an", and "the" include plural referents unless the context clearly dictates otherwise.

DETAILED DESCRIPTION OF THE PRESENT INVENTION

Figure 1A:
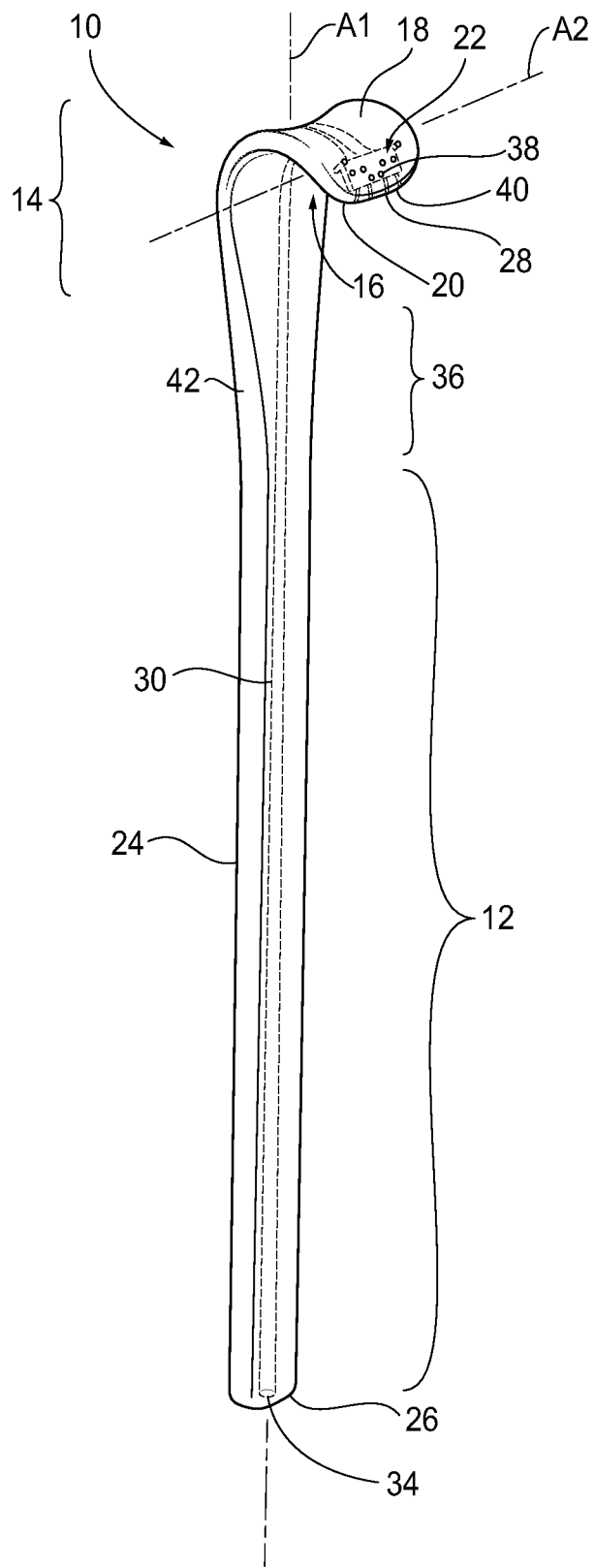
FIG. 1A is a perspective view of an embodiment of an eyelid retractor and irrigation tool.

For purposes of the description hereinafter, the terms "upper", "lower", "right", "left", "vertical", "horizontal", "top", "bottom", "lateral", "longitudinal," and derivatives thereof shall relate to the invention as it is oriented in the drawing figures. The term "proximal" as used herein refers to a portion of an object that is configured to be grasped or manipulated by a user. For example, a proximal end of a tool refers to an end of the tool that is grasped by a user. The term "distal" refers to a portion of the object opposite the proximal potion of the object. For example, the "distal" end of a tool may refer to an end that is farthest away from the user's hand during conventional operation of the tool. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

With reference to the figures, the present disclosure is directed to tools 10, 210, 310 for irrigating or flushing the eyeball and eyelid to remove chemicals, debris, and other irritants from the eye. The tools 10, 210, 310 may be configured to direct fluids (e.g., liquids or gas) towards the inner portion of the eyelid, referred to as the palpebral conjunctiva. The tools 10, 210, 310 may also direct liquid to other portions of the conjunctiva, such as the bulbar conjunctiva and conjunctival fornix. The tools 10, 210, 310 may also direct liquid towards portions of the eyeball, such as the cornea. In some examples, the tools 10, 210, 310, are configured to direct a liquid, such as saline solution, towards the eyelid and eyeball, to clean and flush the eyelid and eyeball. In other examples, the tools 10, 210, 310 may provide liquids comprising therapeutic agents, such as agents for reducing eye irritation, towards the eyelid and/or eyeball. In some examples, the tools 10, 210, 310 may also comprise openings or ports for providing suction for the eyelid and/or eyeball to remove fluid and/or debris from the eyeball.

With specific reference to FIGS. 1A-2C, an eyelid retractor and irrigation tool 10 comprises a handle portion 12 defining a longitudinal first axis A1 configured to be grasped by a user. The handle portion 12 can comprise features for enhancing the user's grip, such as texturing, cushioning materials, and/or high friction materials, as are known in the art. The tool 10 further comprises a hook portion 14 for retracting the eyelid extending from the handle portion 12. The hook portion 14 can comprise an inwardly facing wall 16 and an outwardly facing wall 18. The walls 16, 18 are curved about a second axis A2, which is distinct from the first axis A1. As used herein, an axis may be "distinct from" another axis, when it is not co-linear with the other axis. For example, the axis A1 may be spaced apart from the axis A2, along an entire length of the axes. The axis A1 may also intersect the axis A2, at a single point along the axes. The axis A1 may also be parallel to the axis A2. As used herein, the inwardly facing wall 16 refers to the wall positioned on a radially inward side of the hook portion 14 relative to the second axis A2. The outwardly facing wall 18 is radially outward relative to the inwardly facing wall 16. The hook portion 14 further comprises an edge wall 20 extending between the inwardly facing wall 16 and the outwardly facing wall 18 and an interior cavity 22 defined by the walls 16, 18, 20. The outwardly facing wall 18 may have a curvature that generally conforms to the shape of the eyeball. The tool 10 further comprises an opening 38 or openings extending through the inwardly facing wall 16 and/or the outwardly facing wall 18. Each opening 38 is distanced from and distinct from the edge wall 20. The opening(s) 38 are fluidly connected to the interior cavity 22 and are positioned such that fluid in the interior cavity 22 passes through the opening(s) 38 towards the eyelid and/or eyeball to irrigate the eyelid or eyeball, including the inner surface of the eyelid. For example, when the tool 10 is used to retract the eyelid, liquid may pass through the opening(s) 38 in the inwardly facing wall 16 towards the palpebral conjunctiva. Liquid may pass through the opening(s) 38 in the outwardly facing wall 18 towards the bulbar conjunctiva and/or cornea of the eyeball.

In some examples, the tool 10 comprises or is formed from an elongated member, indicated generally by reference number 24, which forms the handle portion 12 and the hook portion 14. The elongated member 24 can be any convenient size, which can be easily manipulated by a user. The hook portion 14 should be sized to fit within the conjunctival fornix and/or between the eyelid and eyeball. For example, the elongated member 24 may be from about 5 cm to about 15 cm in length. The handle portion 12 may be from about 5 mm to about 15 mm wide. The hook portion 14 may be slightly wider than the handle portion 12. For example, the hook portion 14 may be about 10 mm to about 20 mm wide.

As shown in FIGS. 1A-2C, the elongated member 24 can be an integrally formed or molded structure comprising a proximal end 26 near the handle portion 12 and a distal end 28 on the edge wall 20 of the hook portion 14. The elongated member 24 can be formed from any suitable rigid biocompatible material, such as molded plastics, metals, and ceramics, as are known in the art. In other examples, the handle portion 12 and the hook portion 14 may be separately formed structures connected together by a suitable adhesive or fastener.

Figure 1B:
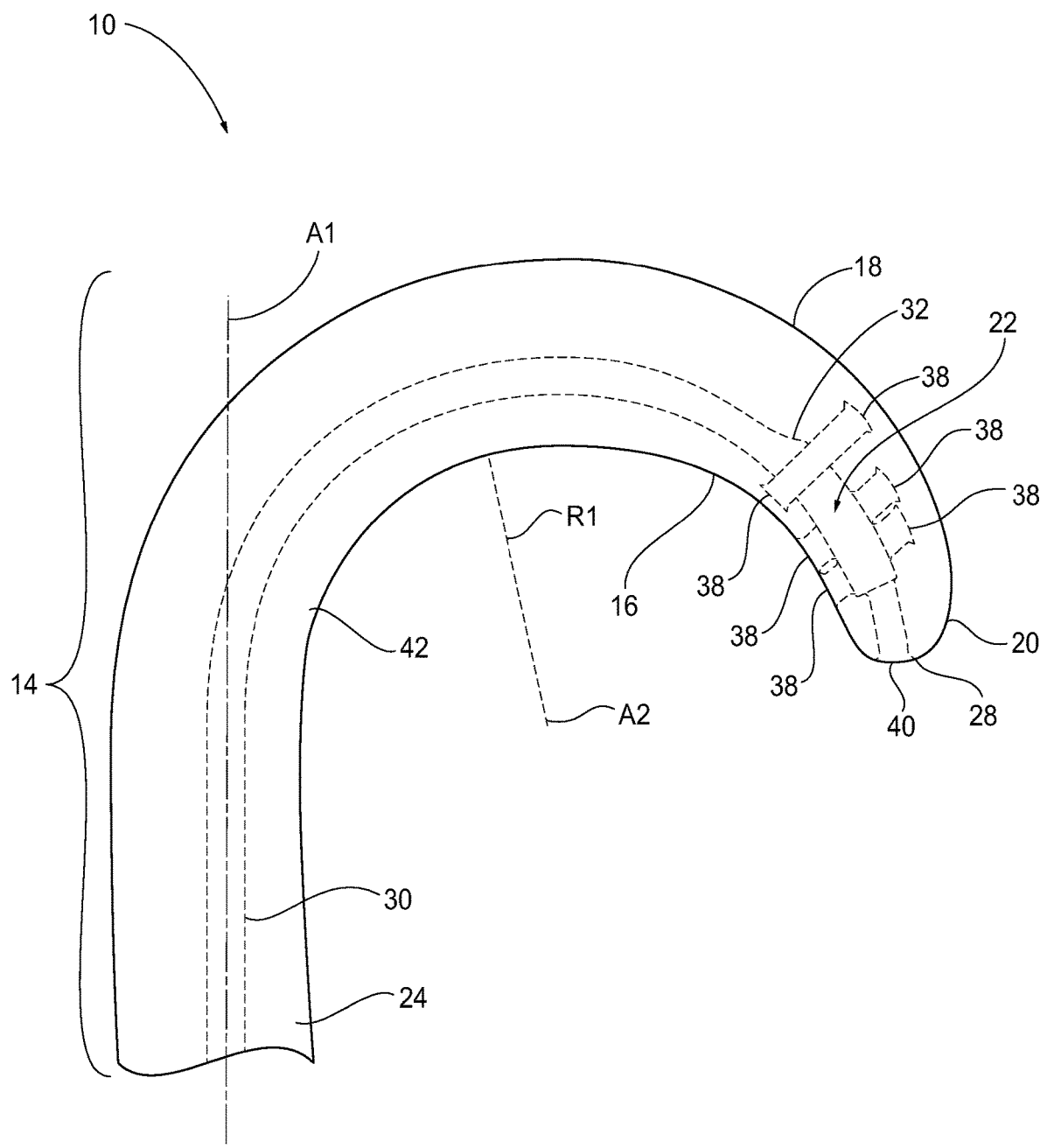
FIG. 1B is a side view of a hook portion of the tool of FIG. 1A.
Figure 1C:
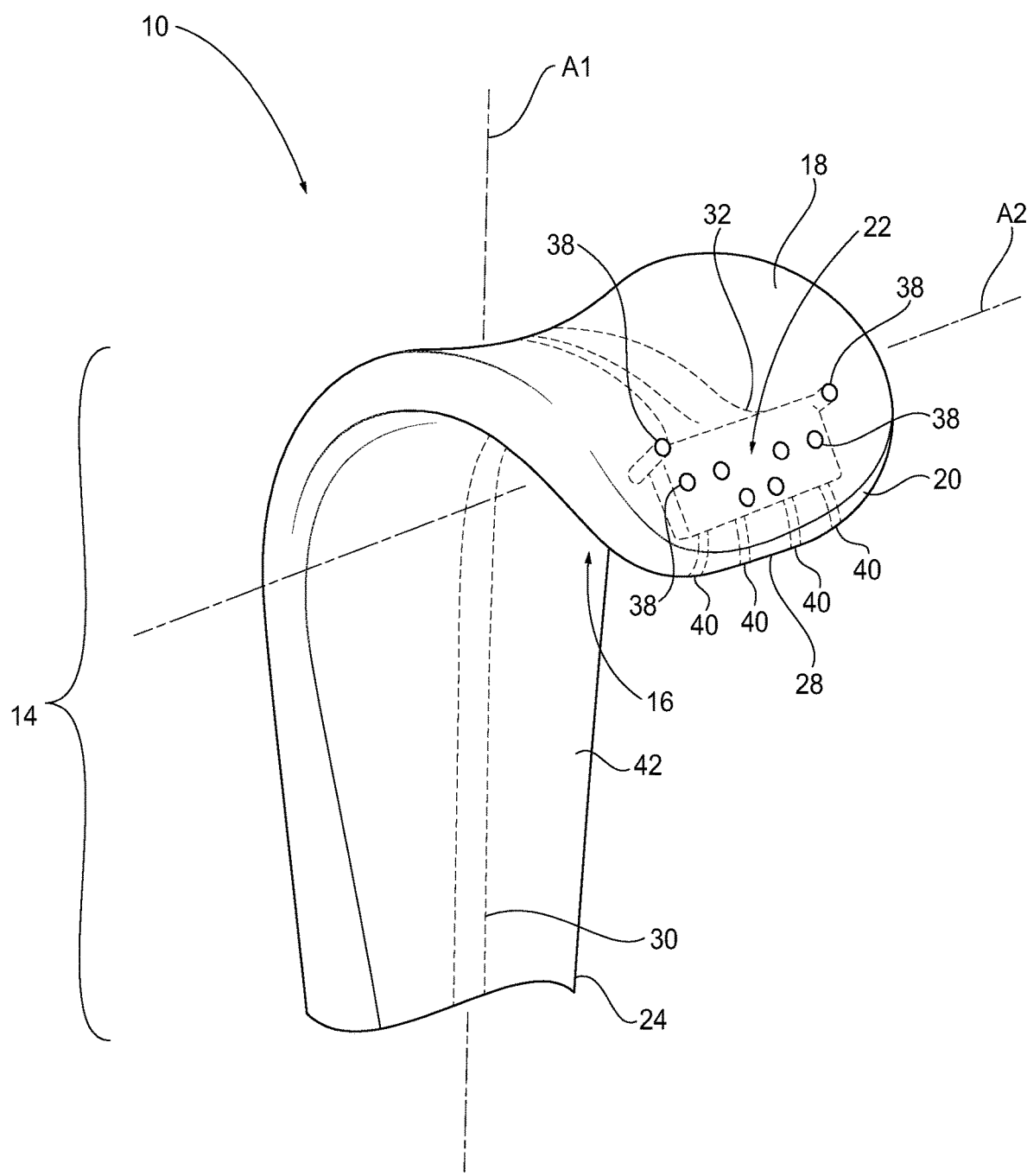
FIG. 1C is an enlarged perspective view of the hook portion of the tool of FIG. 1A.

In some examples, the elongated member 24 defines or is connected to a fluid channel 30 extending through the handle portion 12 and/or the hook portion 14. The fluid channel 30 is sized to deliver a sufficient amount of liquid to the eyelid and/or eyeball for cleansing or for therapeutic purposes. For example, the fluid channel 30 may be about 3 mm to about 10 mm in diameter. As shown in FIGS. 1A-1D, the fluid channel 30 is in fluid communication with the interior cavity 22 of the hook portion 14. For example, the fluid channel 30 may include a tapered section 32, which extends between the interior cavity 22 and the fluid channel 30. As shown in FIGS. 1B and 1C, the interior cavity 22 is a box shaped volume comprising a substantially rectangular cross section. The fluid channel 30 can also comprise a first or proximal end 34, opposite the tapered section 32, which extends through the proximal end 26 of the elongated member 24. In some examples, the handle portion 12 and/or the hook portion 14 of the elongated member 24 can comprise a hollow tube comprising an annular sidewall 42, which defines the fluid channel 30. In some examples, the handle portion 12 and/or hook portion 14 comprise a polygonal cross section, such as a square cross section, while the fluid channel 30, which extends through the polygonal cross section, has a circular cross section. In other examples, the fluid channel 30 may be a separate conduit, hose, or tube connected to the handle portion 12 and/or the hook portion 14.

In some examples, the elongated member 24 further comprises a neck or intermediate portion 36 extending between the handle portion 12 and the hook portion 14. In some examples, the intermediate portion 36 is the same dimensions (e.g., has the same cross-section) as the handle portion 12. The intermediate portion 36 may also define a longitudinal axis, which is co-linear with the longitudinal axis A1 of the handle portion 12. The intermediate portion 36 may taper between the distal end and the proximal end thereof. In that case, as shown in FIG. 1A, a width of the hook portion 14 is greater than a width of the handle portion 12. The intermediate portion 36 may comprise a polygonal shaped cross section to improve maneuverability and/or for aesthetic purposes.

Figure 1D:
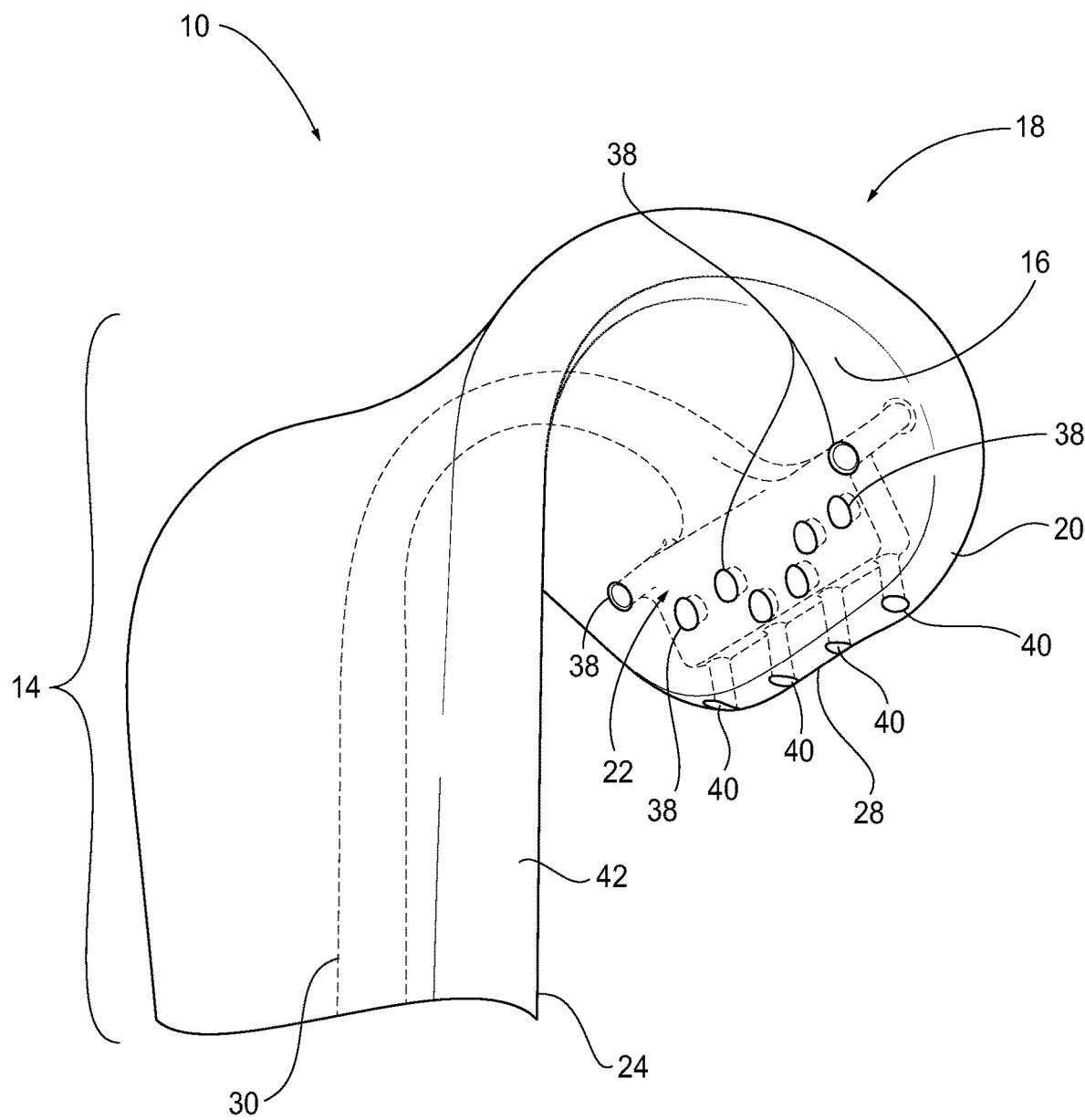
FIG. 1D is a perspective view of the hook portion of the tool of FIG. 1A rotated clockwise by 90° about the longitudinal axis when viewed from the top of the tool.
Figure 2A:
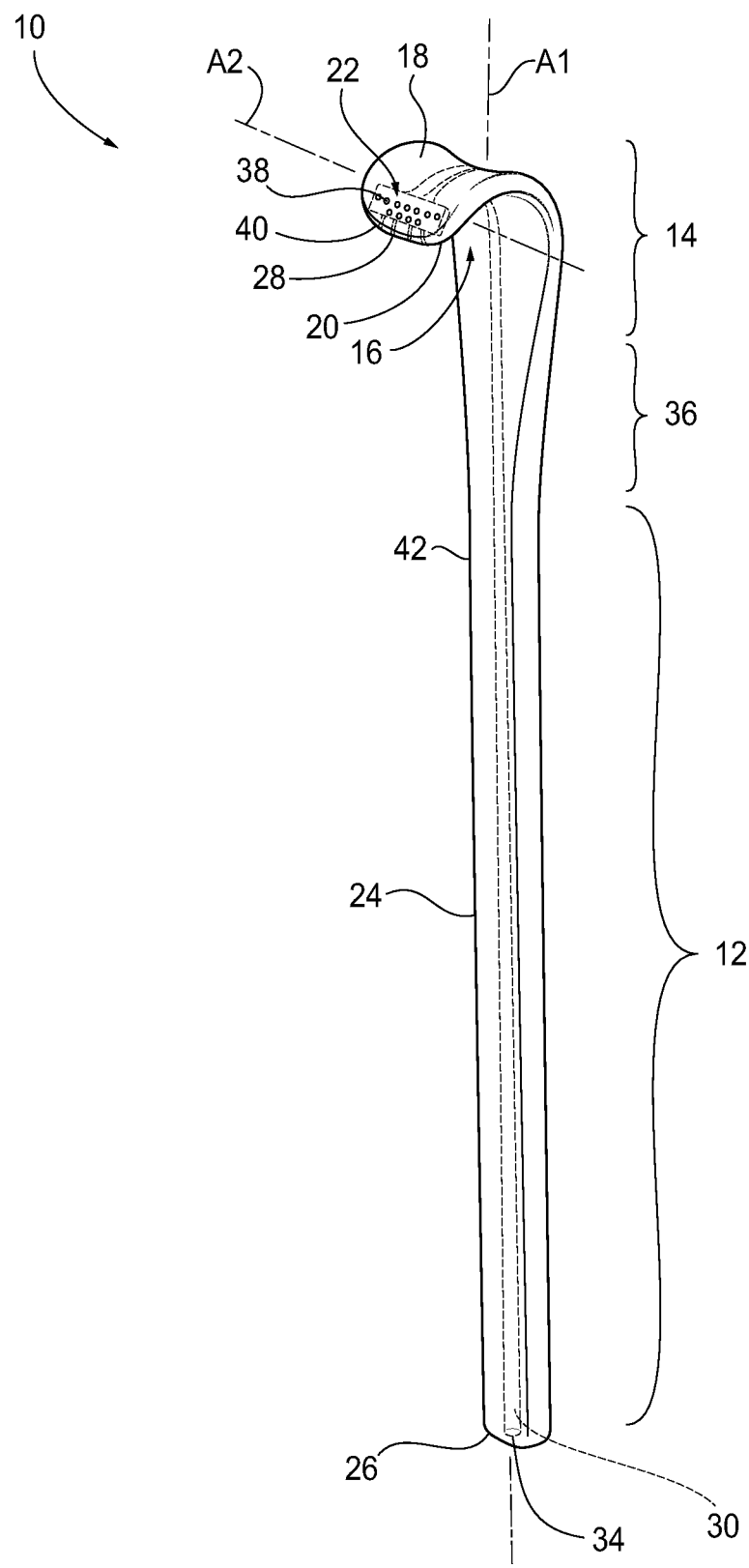
FIG. 2A is a drawing of a perspective view of another embodiment of an eyelid retractor and irrigation tool.
Figure 2B:
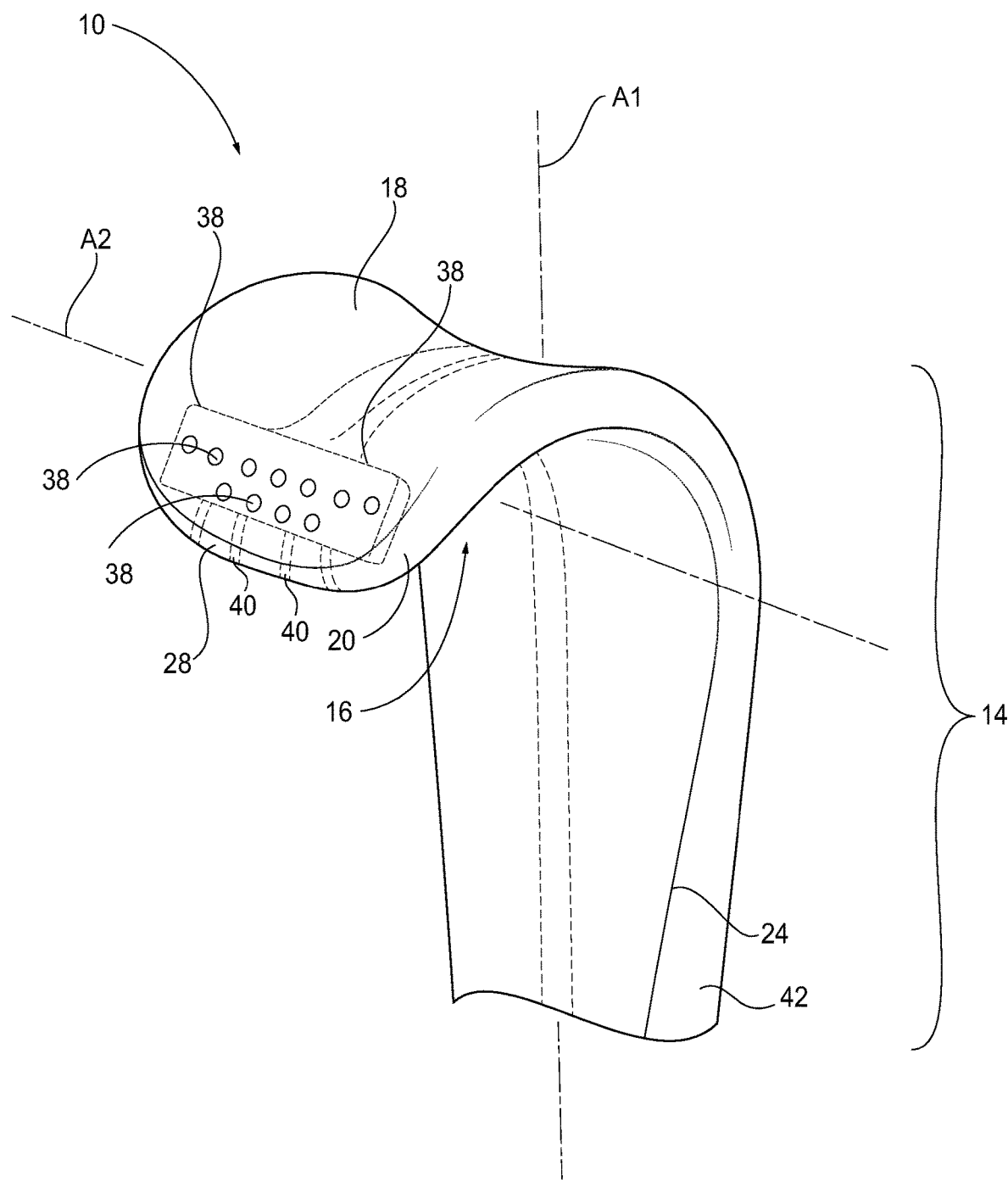
FIG. 2B is an enlarged view of the hook portion of FIG. 2A.
Figure 2C:
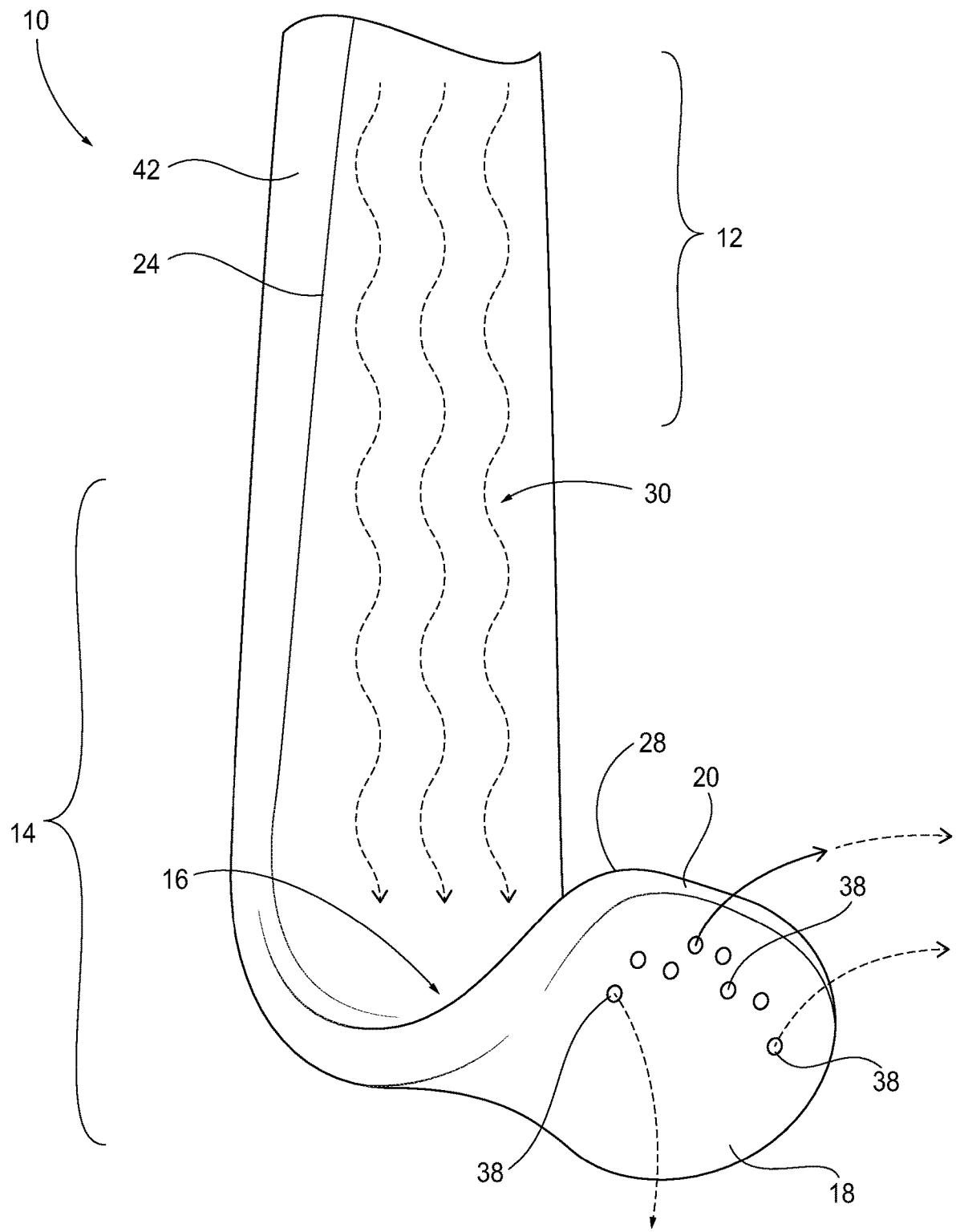
FIG. 2C is a drawing of the hook portion of the tool of FIG. 2A, showing liquid being expelled from the tool.

The hook portion 12 of the tool 10 may comprise or define an arcuate profile, when viewed from the side, as shown in FIG. 1B. The arcuate profile may be any suitable size for grasping the eyelid, while at the same time generally conforming to the shape of the eyeball. In some examples, the tool may be sold in a variety of sizes for use with different sized patients. The arcuate profile may have a radius R1 of from about 5 mm to about 10 mm, or preferably about 8 mm. The hook portion 14 may also have a curved or partially curved edge wall, as shown in FIGS. 1C and 1D, so that the hook portion 14 can be easily positioned under the eyelid.

As discussed previously, the hook portion 14 includes the opening(s) 38 extending through either the inwardly facing wall 16 or the outwardly facing wall 18. The opening(s) 38 can be any convenient size and shape sufficient for introducing liquid to the eyelid and eyeball. For example, the opening(s) 38 can be a circular or elliptical shape. The opening(s) 38 can be about 0.5 mm to about 3 mm in diameter and/or can have an area of from about 0.2 mm² to about 7 mm². As shown in FIGS. 1C and 1D, in some examples, the hook portion 14 may comprise sixteen openings 38 (eight openings 38 extending through the inwardly facing wall 16 and eight openings 38 extending through the outwardly facing wall 18). In other examples, the walls 16, 18 may comprise from five to ten openings 38. A total area of all opening(s) 38 on the inwardly facing wall 16 and/or the outwardly facing wall 18 may be about 1.0 mm² to about 70 mm².

In other examples, the opening(s) 38 may comprise elongated slots, perforations, or other liquid permeable structures. In some examples, the hook portion 14 comprises openings 38 on both the inwardly facing wall 16 and the outwardly facing wall 18, as shown in FIGS. 1A-1D. The hook portion 14 may further comprise an opening 40 or openings extending from the interior cavity 22 through the edge wall 20. As discussed previously, the opening(s) 38 extending through the inwardly and outwardly facing walls 16, 18 are positioned to provide liquid to portions of the conjunctiva. The opening(s) 40 on the edge wall 20 are positioned to provide liquid to portions of the eyeball, such as to the cornea. The opening(s) 40 may also be about 0.5 mm to about 3 mm in diameter and/or can have an area of from about 0.2 mm² to about 7 mm². As shown in FIG. 1D, the hook portion 14 includes four openings 40. In other examples, the hook portion 14 may include from two to eight openings 40. A total area of all openings 40 on the hook portion 14 may be from about 0.5 mm² to about 50 mm².

The opening(s) 38, 40 may be provided on the walls 16, 18, 20 in any convenient pattern or arrangement sufficient for providing liquid to various regions of the eyeball and eyelid. For example, opening(s) 38 on the inwardly facing wall 16 and the outwardly facing wall 18 can be aligned in one or more rows extending substantially parallel to the axis A2 defined by the curvature of the hook portion 14, as shown for example, in the embodiment in FIGS. 2A and 2B. Alternatively, openings 38 can be positioned on the inwardly facing wall 16 and/or the outwardly facing wall 18 in an offset pattern, in which a center of each opening 38 is not aligned with a center of another opening 38 in either a longitudinal and/or axial direction, as shown in FIGS. 1C and 1D. In other examples, the opening(s) 38 may be positioned about a curved virtual line or in any other convenient pattern. In some examples, each opening 38 on the outwardly facing wall 18 is aligned with a corresponding opening 38 on the inwardly facing wall 16. In other examples, openings 38 on the inwardly facing wall 16 and the outwardly facing wall 18 are offset from each other.

Figure 3:
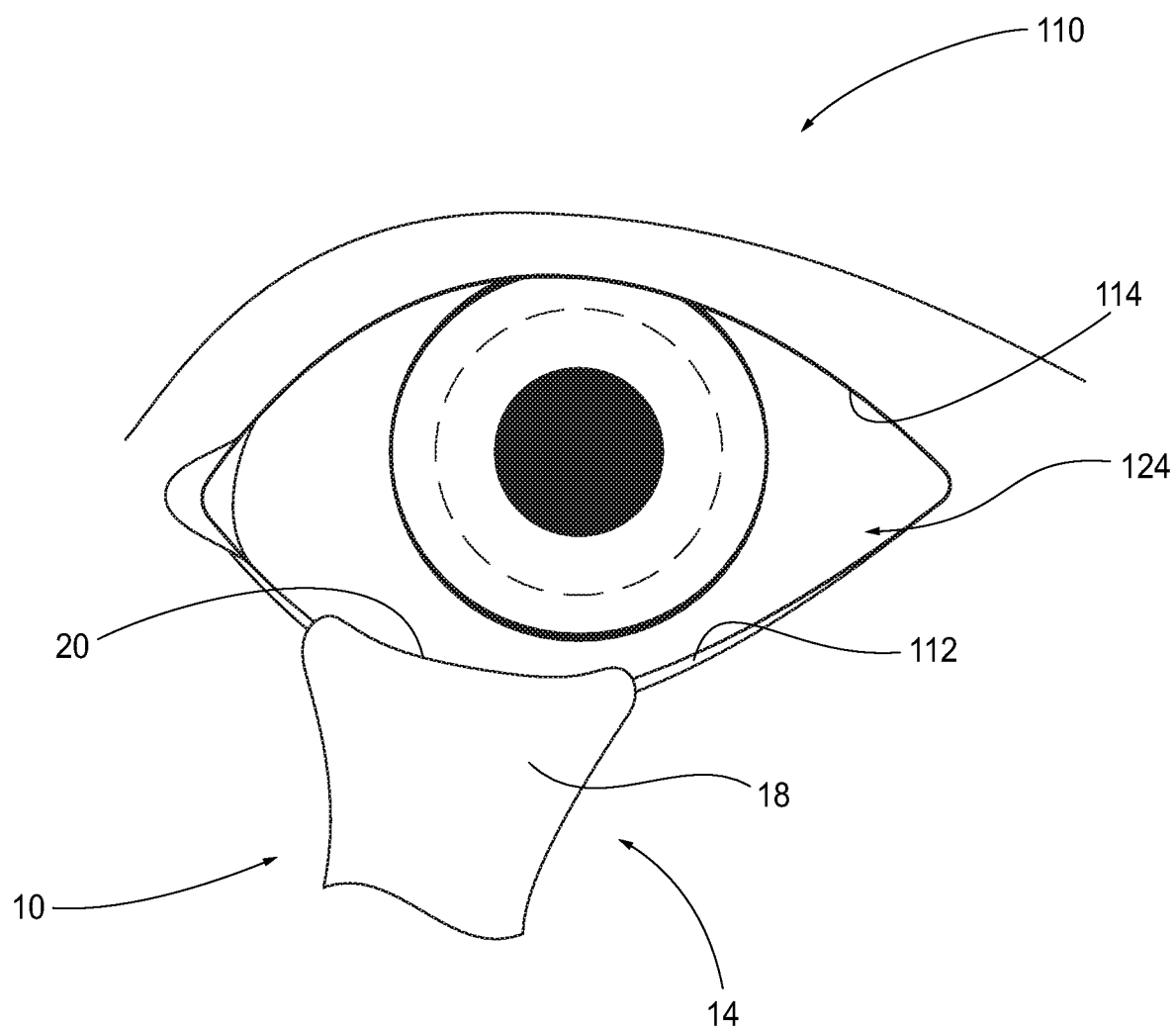
FIG. 3 is a drawing showing an eyelid retractor and irrigation tool engaged to a lower eyelid of a patient to retract the lower eyelid.
Figure 4:
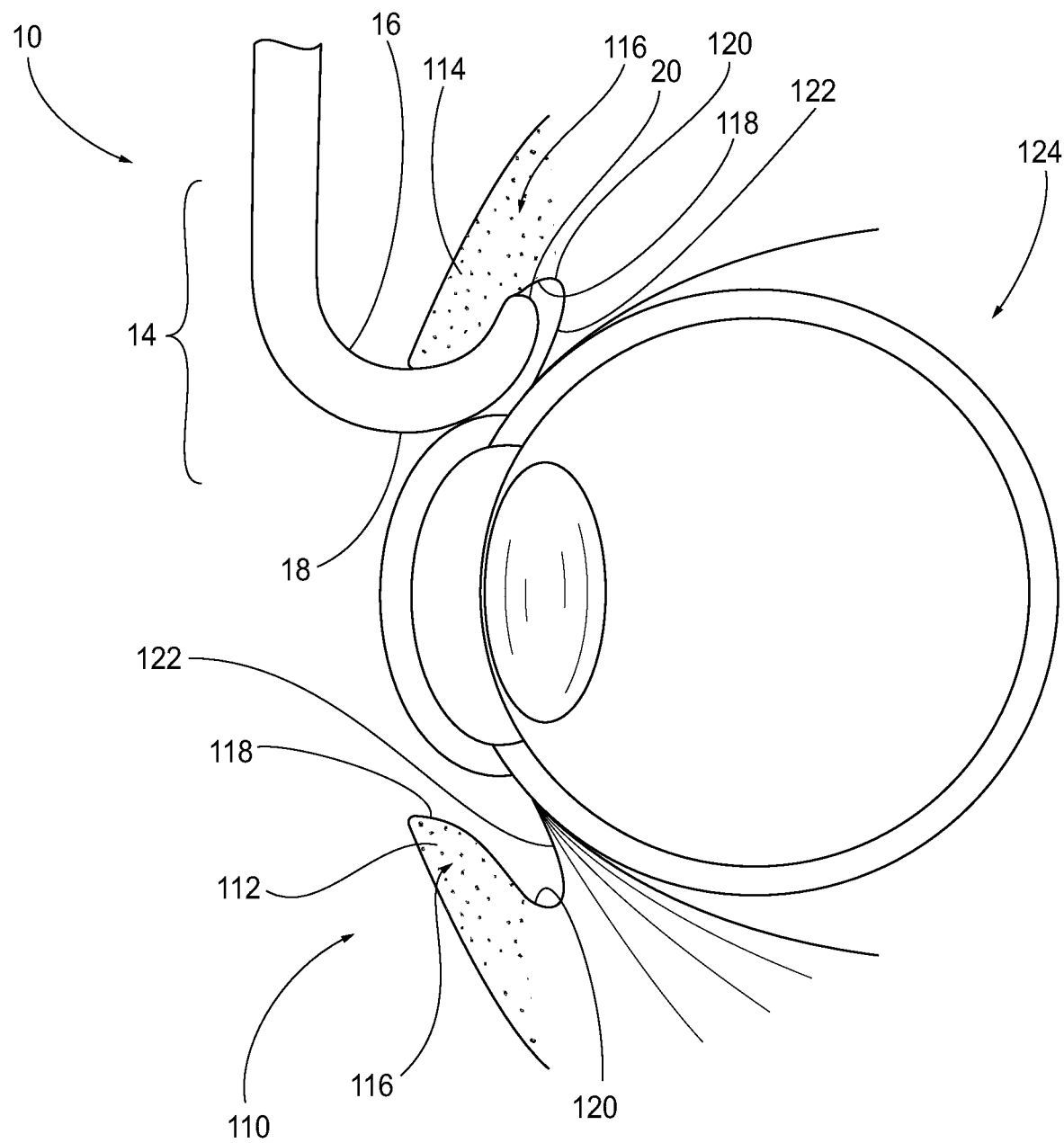
FIG. 4 is a drawing of a cross-section of an eye of a patient showing the eyelid retractor and irrigation tool engaged to an upper eyelid of the patient, to retract the upper eyelid.

FIGS. 3 and 4 show the tool 10, in use, retracting an eyelid 112, 114 of an eye 110. Specifically, FIG. 3 shows the tool 10 engaged with and retracing the lower eyelid 112. FIG. 4 shows the tool 10 engaged with and retracting the upper eyelid 114. As shown in FIG. 4, the inwardly facing wall 16 of the hook portion 14 extends around the conjunctiva 116 and contacts the inner surface of the upper eyelid 114, referred to as the palpebral conjunctiva 118. The outwardly facing wall 18 and/or edge wall 20 of the hook portion 14 contacts or is adjacent to the conjunctival fornix 120 and/or the bulbar conjunctiva 122. The outwardly facing wall 18 may also be positioned adjacent to portions of the surface of the eyeball 124, such as the cornea.

Figure 5:
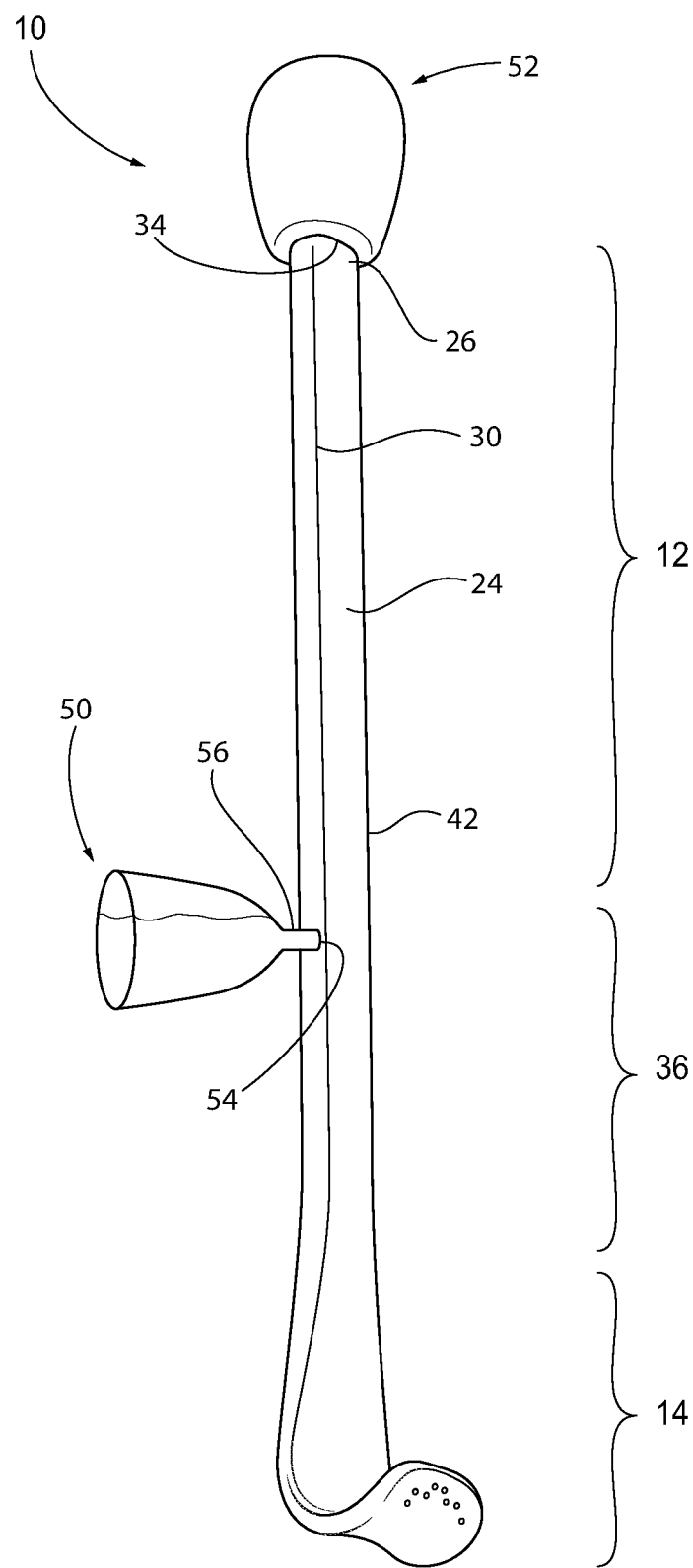
FIG. 5 is a schematic drawing of another embodiment of an eyelid retractor and irrigation tool including a fluid container and fluid dispensing bulb.

With reference to FIG. 5, in some examples, the tool 10 further comprises a liquid container 50, such as a vial, and a compressible bulb 52 mounted to the elongated member 24 for introducing fluid (e.g., a liquid or gas) into the fluid channel 30. The container 50 and/or bulb 52 may contain a fluid volume of about 15 mL. The liquid container 50 can be connected to the fluid channel 30 through an opening 54 in the sidewall 42 of the elongated member 24. The opening 54 may be about 3 mm to about 5 mm in diameter and/or may have an area of about 5 mm² to about 20 mm².

The opening 54 can be positioned in the handle portion 12 near the middle of the elongated member 24, as shown in FIG. 5, or at any other convenient location on the elongated member 24. The fluid container 50 can be a rigid container comprising a narrow spout or nozzle 56 connected to the opening 54. Fluid may flow through the nozzle 56 into the fluid channel 30 by gravity. Also, fluid may be drawn into the fluid channel 30 by suction, when portions of the fluid channel 30 are pressurized by, for example, actuating the bulb 52. The liquid container 50 may be filled with saline solution for flushing the eyelid and/or eyeball. Alternatively, the liquid container 50 may be filled with a therapeutic agent, which may be introduced to the eye after flushing. For example, the therapeutic agent may relieve irritation. The bulb 52 can be configured to push gas, such as air, through the fluid channel 30.

As shown in FIG. 5, the bulb 52 can be mounted to the proximal end 26 of the elongated member 24, such that gas from the bulb 52 is introduced into the fluid channel 30 through the proximal end 34 of the fluid channel 30. The compressible bulb 52 can be a flexible bulbous structure formed from synthetic rubber or another suitable material that comprises or defines an interior in fluid communication with the fluid channel 30. Compressing the bulb 52 pressurizes the fluid channel 30 and/or pushes gas into the fluid channel 30, which pushes liquid through the fluid channel 30 to the interior cavity 22 and opening(s) 38 in the hook portion 14. In other examples, the bulb 52 can be mounted to other convenient locations on the elongated member 24. For example, the bulb 52 may be mounted to the sidewall 42 of the elongated member 24 and configured to introduce gas into the fluid channel 30 through another opening in the sidewall 42.

Figure 6:
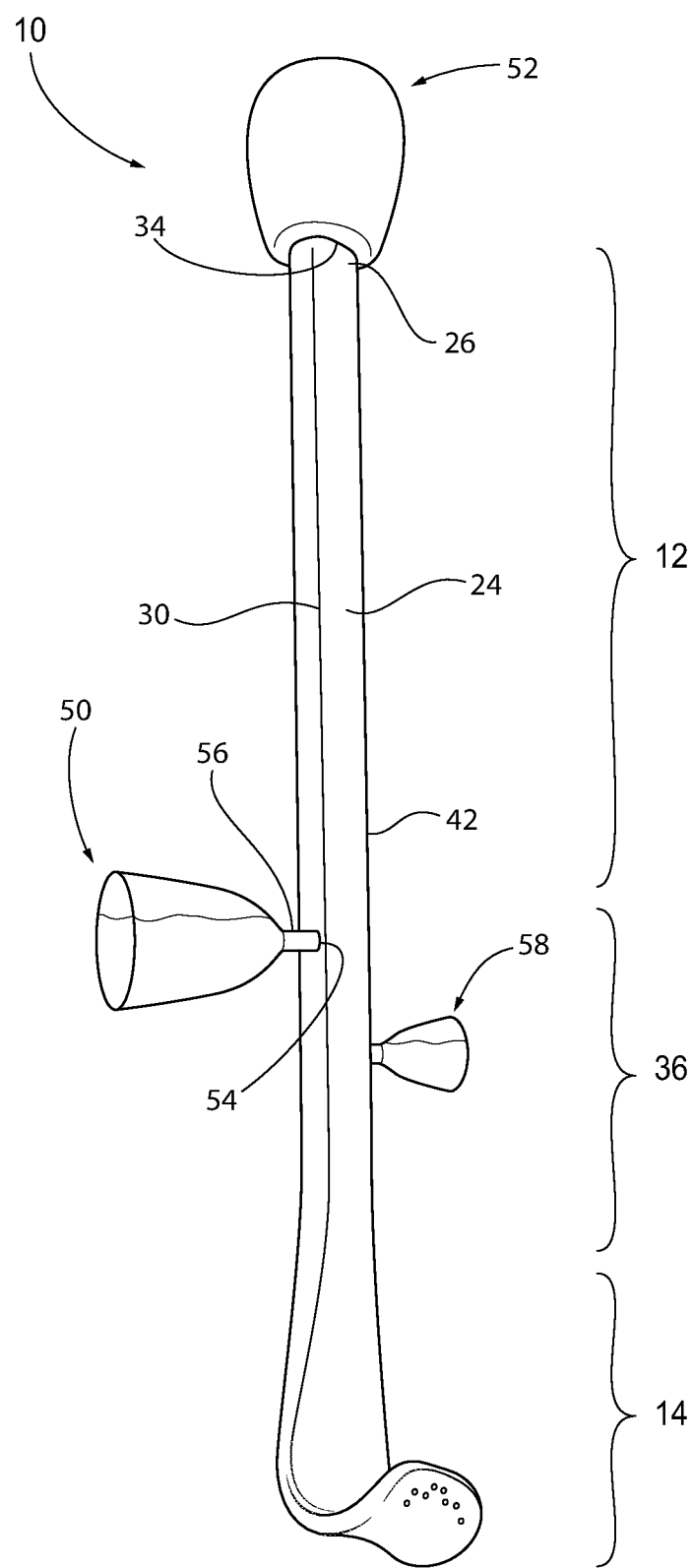
FIG. 6 is a schematic drawing of another embodiment of an eyelid retractor and irrigation tool including multiple fluid containers and a fluid dispensing bulb, according to an aspect of the disclosure.

With reference to FIG. 6, another example of a tool 10 includes a first liquid container 50 and the compressible bulb 52 previously described. The tool 10 further comprises a second liquid container 58 mounted to the elongated member 24 at a position different from the position of the first liquid container 50. For example, as shown in FIG. 6, the second liquid container 58 may be positioned in the middle of the elongated member 24 on an opposite side of the elongated member 24 from the first liquid container 50. The first liquid container 50 may be filled with saline solution for flushing the eyelid and/or eye. The second liquid container 58 may be filled with a therapeutic agent, which may be introduced to the eye after flushing.

Figure 7:
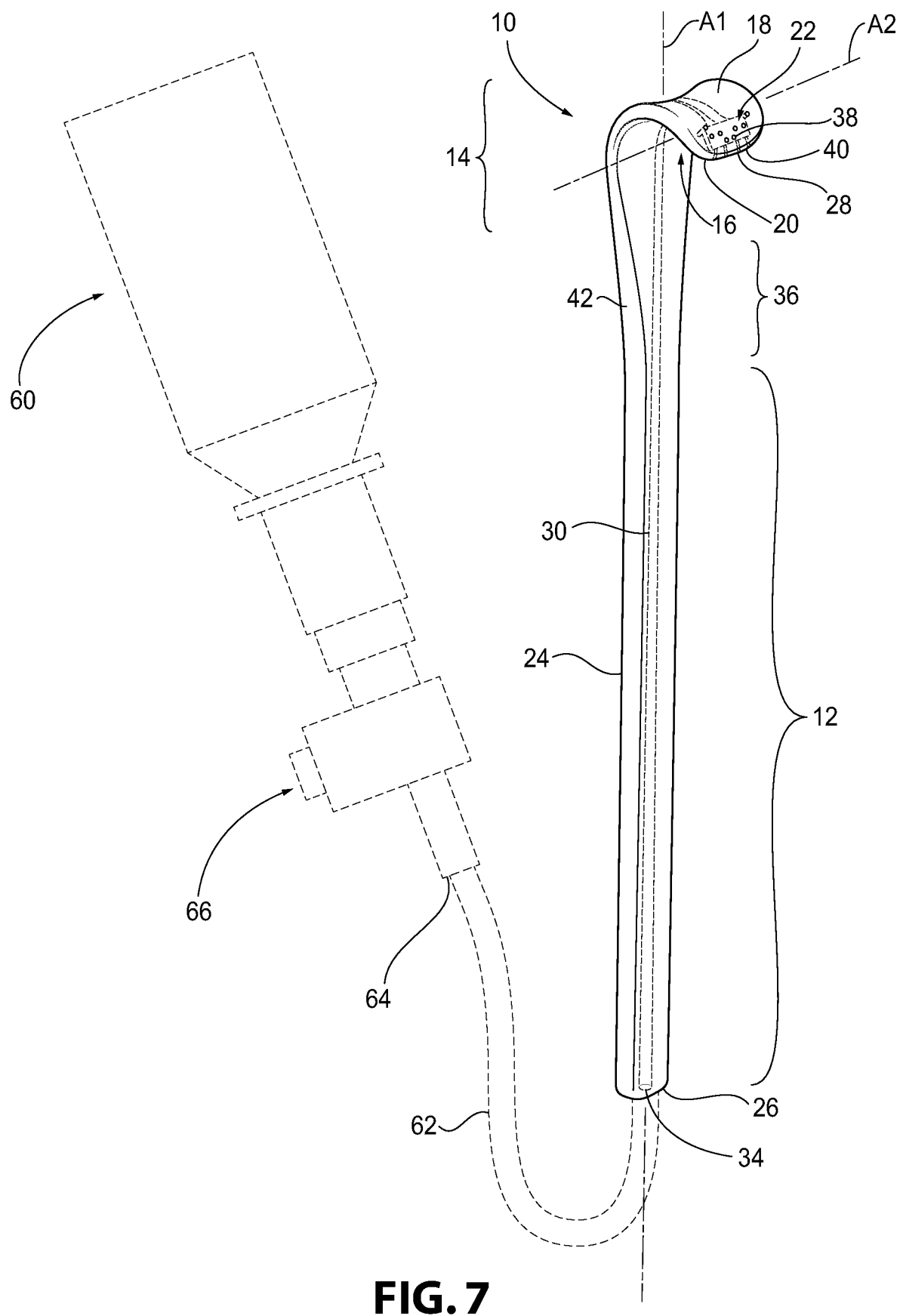
FIG. 7 is a schematic drawing of an eyelid retractor and irrigation tool connected to a liquid-dispensing bottle, according to an aspect of the disclosure.

With reference to FIG. 7, in other examples, an eyelid retractor and irrigation tool 10 comprises or is connected to a liquid bottle 60 by a fluid conduit, such as a segment of flexible tube 62. For example, the tube 62 may be in fluid communication with and extend from the proximal end 34 of the fluid channel 30 to a port or nozzle 64 of the liquid bottle 60. The liquid bottle 60 can be a conventional liquid-containing bottle formed from a flexible material. The bottle 60 can be compressed by a user to force the liquid from the bottle 60 into the tube 62 and through the fluid channel 30 of the tool 10. In other examples, as shown in FIG. 7, the bottle 60 may comprise a valve 66, such as a stopcock valve. The valve 66 may also be positioned in the tube 62 between the bottle 60 and the fluid channel 30 of the tool 10. The valve 66 can be opened to control fluid dispensed from the bottle 60 into the tube 62. For example, the liquid bottle 60 may be held in an inverted and elevated position, such that liquid in the bottle 60 flows through the port or nozzle 64 and into the tube 62 by gravity. When the user is ready to provide liquid to the eye and/or eyelid through the tool 10, the user opens the valve 66, allowing the liquid to flow from the bottle 60, past the open valve 66, and into the fluid channel 30 of the tool 10. When a sufficient amount of liquid has been provided to the eyeball and eyelid, the user can close the valve 66 to stop the flow of liquid from the bottle 60.

Figure 8:
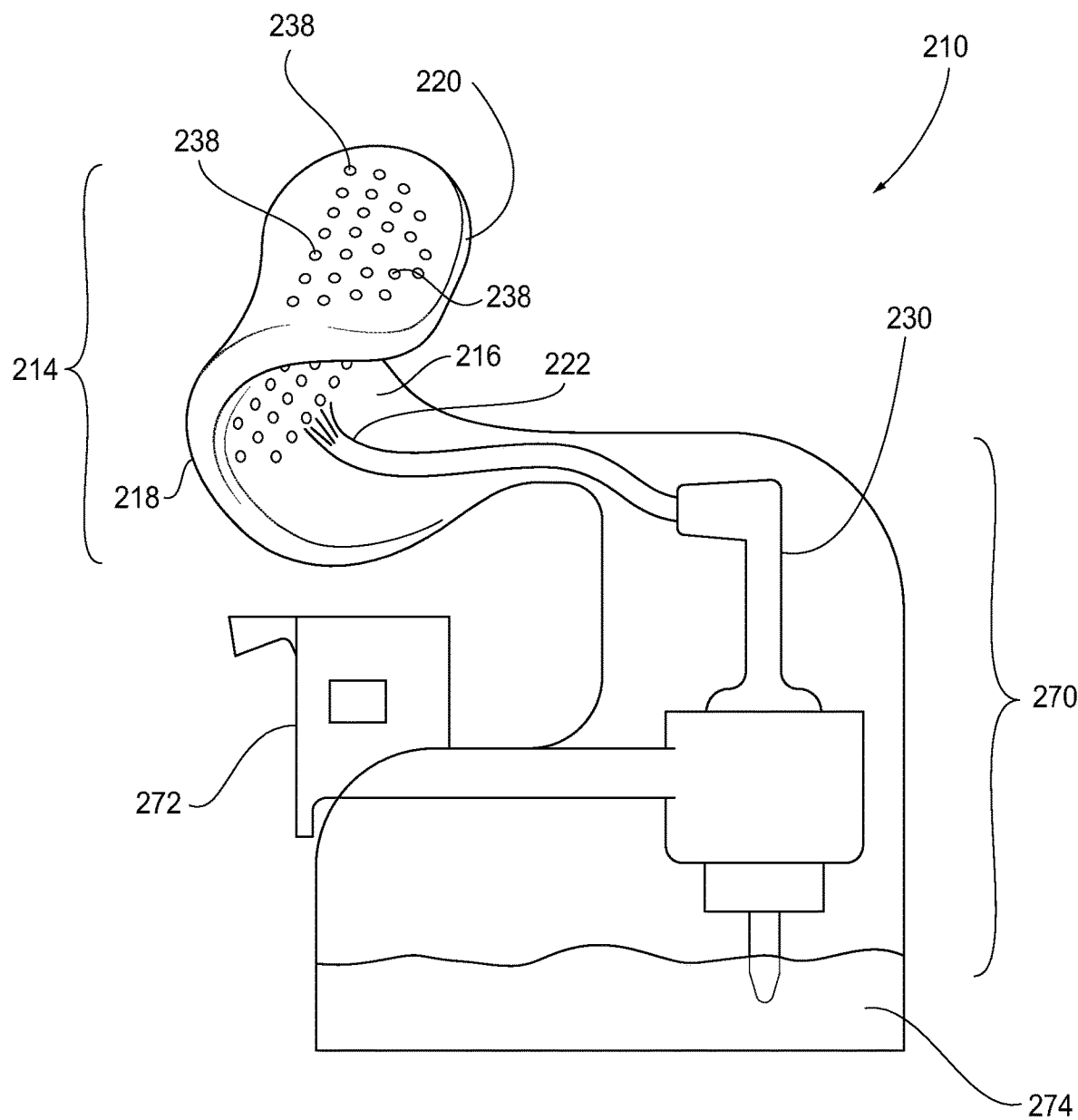
FIG. 8 is a schematic drawing of another embodiment of an eyelid retractor and irrigation tool including a trigger for dispensing liquid, according to an aspect of the disclosure.

With reference to FIG. 8, another example of an eyelid retracting and irrigating tool 210, includes a hook portion 214, a fluid containing portion 270, and a trigger 272 for expelling liquid contained in the tool 210 towards the eyelid and/or eyeball through the hook portion 214. The hook portion 214 is generally similar in size and shape to hook portions of previously described examples. For example, the hook portion 214 may comprise the inwardly facing wall 216 and the outwardly facing wall 218. The walls 216, 218 may be curved about an axis, which is distinct from a central longitudinal axis of other portions of the tool 210. As before, the wall 218 is shaped to generally conform to the shape of the eyeball. The hook portion 214 may further comprise the edge wall 220 extending between the inwardly and outwardly facing walls 216, 218 and an interior cavity 222 defined by the walls 216, 218, 220.

The hook portion 214 may further comprise opening(s) 238 extending through the inwardly facing wall 216 and/or the outwardly facing wall 218. As in previous examples, the opening(s) 238 can be fluidly connected to the interior cavity 222 and positioned such that fluid in the interior cavity passes through the opening(s) 238 to irrigate the eyeball and/or the eyelid.

The fluid containing portion 270 replaces the handle portions, liquid containers, and compressible bulbs described in previous examples. The fluid containing portion 270 may comprise a fluid reservoir 274 configured to contain a liquid. The liquid may be a flushing solution, such as saline solution, or a therapeutic agent. The fluid containing portion 270 further comprises a fluid channel 230 extending from the reservoir 274 to the interior cavity 222 of the hook portion 214 for conducting fluid from the reservoir 274 to the opening(s) 238 of the hook portion 214.

The tool 210 further comprises the trigger 272. The trigger 272 may be similar in shape and function to a trigger 272 of a water gun. For example, the trigger 272 may be coupled to a pump or piston for drawing liquid from the reservoir 274 (e.g., as the trigger extends) and ejecting the liquid into the fluid channel 230 (e.g., as the pump or piston is compressed). Alternatively, the trigger 272 may be configured to actuate other mechanical and/or electrical devices configured to draw liquid from the reservoir 274 to the fluid channel 230, as are known in the art.

Figure 9:
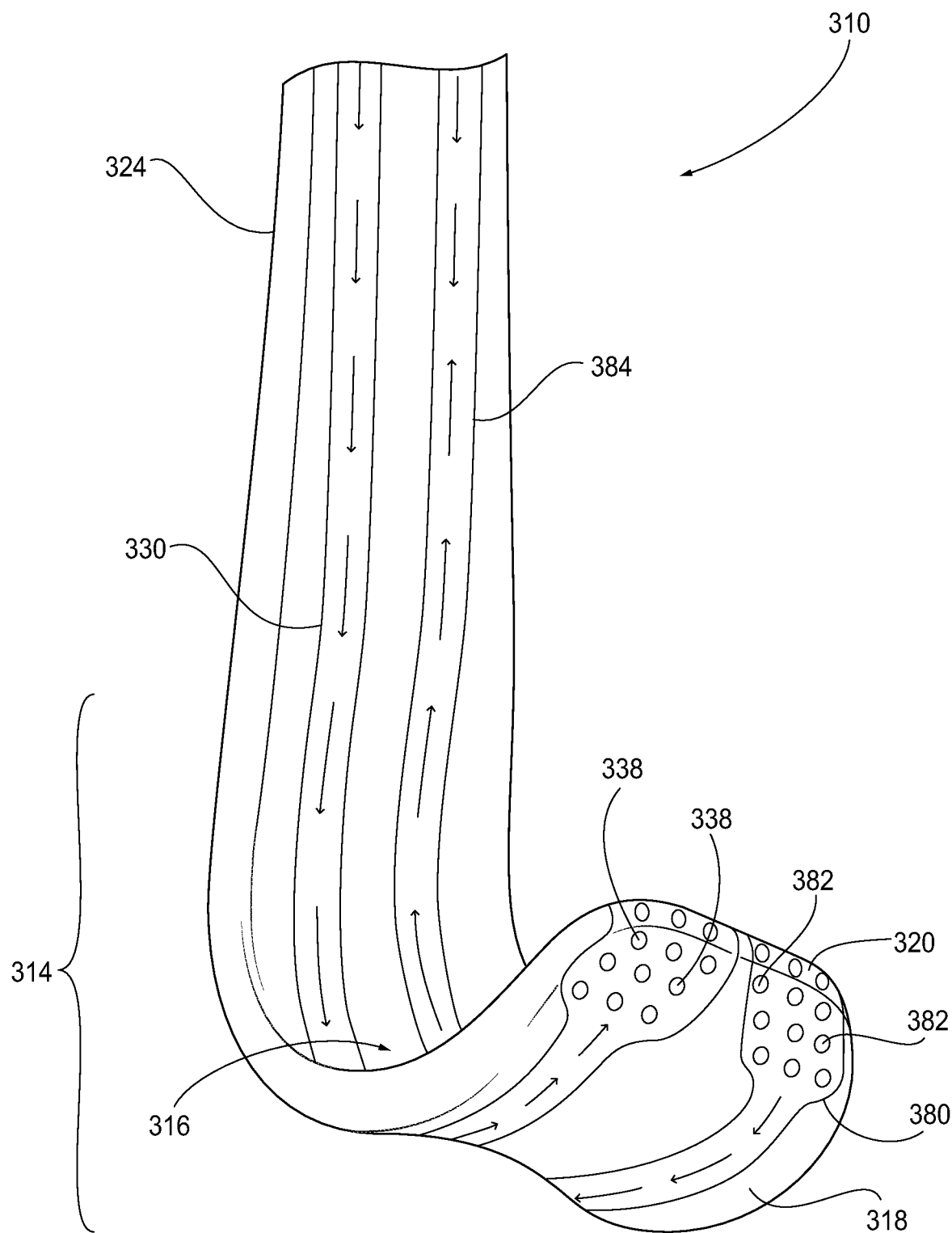
FIG. 9 is a schematic drawing of another embodiment of a hook portion of an eyelid retractor and irrigation tool, according to an aspect of the disclosure.

With reference to FIG. 9, another example of an eyelid retracting and irrigation tool 310 including a hook portion 314 is shown. As will be appreciated by those skilled in the art, many of the previously described examples of tools can be adapted to include the hook portion 314, shown in FIG. 9. As in previous examples, the hook portion 314 comprises the inwardly facing wall 316 and the outwardly facing wall 318. The walls 316, 318 may be curved about an axis, which is distinct from a central longitudinal axis of other parts of the tool 310. As before, the outwardly facing wall 318 is shaped to generally conform to the shape of the eyeball. The hook portion 314 may further comprise an edge wall 320 extending between the inwardly and outwardly facing walls 316, 318.

Unlike in previous examples, in which the walls define a single interior cavity, the hook portion 314 includes two cavities, namely a first interior cavity 314 and a second interior cavity 380. The hook portion 314 further comprises opening(s) 338 extending through the inwardly facing wall 316 and/or the outwardly facing wall 318 in fluid communication with the first interior cavity 322. The first interior cavity 322 can also be in fluid communication with a first fluid channel 330 extending from the hook portion 314 through an elongated member 324 of the tool 310. In some examples, the opening(s) 338 are configured to provide liquid to the eyeball and/or eyelid. For example, as in previous examples, liquid may pass from the first fluid channel 330 to the opening(s) 338 through the first interior cavity 322.

The hook portion 314 may further comprise second opening(s) 382, which also extend through the inwardly facing wall 316 and the outwardly facing wall 318 of the hook portion 314. The second opening(s) 382 are in fluid communication with the second interior cavity 380. A second fluid channel 384 may be in fluid communication with the second interior cavity 380. In some examples, the second fluid channel 384 is configured to provide vacuum or suction to the second interior cavity 380 and second opening(s) 382.

In use, liquid, such as saline solution or a therapeutic agent, is provided to the eyelid and/or eyeball from the first fluid channel 330 through the first interior cavity 322 and first opening(s) 338. Liquids can then be collected under suction. For example, when vacuum or suction is provided through the second fluid channel 384, fluid collected near the eyelid and/or eyeball, such as fluid collected in the conjunctival fornix, may pass into the second interior cavity 380 through the second opening(s) 382. Collected liquid may pass through the second fluid channel 384 and to a collection device or container for disposal. In this way, liquids can be provided to the eyelid and/or eyeball for cleansing or therapeutic purposes. The dispensed liquids can be removed from the eyelid and/or eyeball under suction through the second opening(s) 382 and second fluid channel 384.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements. Furthermore, it is to be understood that the present invention contemplates that, to the extent possible, one or more features of any embodiment can be combined with one or more features of any other embodiment.

The invention claimed is:

1. An eyelid retractor and irrigation tool, comprising:
   a handle portion defining a longitudinal first axis configured to be grasped by a user;
   a hook portion for retracting an eyelid connected to the handle portion, the hook portion comprising: inwardly and outwardly facing walls, which are curved about a second axis, which is distinct from the first axis; an edge wall extending between the inwardly and outwardly facing walls; and an interior cavity defined between the walls; and
   at least one opening extending through the inwardly facing wall and the at least one opening extending through the outwardly facing wall fluidly connected to the interior cavity and positioned such that fluid in the interior cavity passes through the at least one opening to irrigate portions of an eye including the eyelid;

wherein the at least one opening is distanced from and distinct from the edge wall.

2. The tool of claim 1, wherein the first axis is spaced apart from the second axis along an entire length of the axes.

3. The tool of claim 1, wherein a surface of the outwardly facing wall generally conforms to a shape of an eyeball.

4. The tool of claim 1, wherein the handle portion comprises a fluid channel in fluid communication with the interior cavity of the hook portion.

5. The tool of claim 1, wherein the handle portion comprises an elongated member comprising a fluid channel extending through at least a portion of the handle portion in fluid communication with the interior cavity of the hook portion.

6. The tool of claim 5, wherein at least a portion of the handle portion has a polygonal cross section, and wherein at least a portion of the fluid channel through the polygonal cross section has a circular cross section.

7. The tool of claim 5, wherein the fluid channel comprises a first end at a proximal end of the elongated member and a second end, opposite the first end, which is connected to the interior cavity of the hook portion.

8. The tool of claim 5, further comprising a liquid container mounted to the handle portion, wherein the container comprises an interior in fluid communication with the fluid channel for introducing liquid into the fluid channel to be expelled from the at least one opening extending through the inwardly facing wall or the outwardly facing wall.

9. The tool of claim 8, wherein the handle portion comprises at least one opening extending through a sidewall of the elongated member, and wherein the liquid container comprises an open end connected to the at least one opening of the handle portion, such that liquid from the liquid container is provided into the fluid channel through the at least one opening of the handle portion.

10. The tool of claim 8, further comprising a compressible bulb mounted to the handle portion comprising an interior in fluid communication with the fluid channel, wherein compressing the bulb pushes gas into the fluid channel to expel liquid from the liquid container through the fluid channel to the interior cavity of the hook portion and through the at least one opening of the hook portion.

11. The tool of claim 5, further comprising:
a first liquid container mounted to the handle portion comprising an interior in fluid communication with the fluid channel for introducing a first liquid into the fluid channel through at least one first opening in a sidewall of the elongated member;
a second liquid container mounted to the handle portion comprising an interior in fluid communication with the fluid channel for introducing a second liquid into the fluid channel through at least one second opening in the sidewall of the elongated member; and
a compressible bulb mounted to the handle portion comprising an interior in fluid communication with the fluid channel, wherein compressing the bulb pushes gas into the fluid channel to expel the first liquid and the second liquid from the fluid channel to the interior cavity of the hook portion and through the at least one opening of the hook portion.

12. The tool of claim 11, wherein the compressible bulb is mounted to a proximal end of the elongated member and introduces the gas into the fluid channel through a proximal end of the fluid channel.

13. The tool of claim 1, further comprising an intermediate portion between the handle portion and the hook portion, wherein the intermediate portion is tapered such that a width of the hook portion is greater than a width of the handle portion.

14. The tool of claim 1, wherein the hook portion comprises an arcuate profile with a radius of from 5 mm to 10 mm.

15. The tool of claim 1, wherein the hook portion comprises at least one opening extending from the interior cavity through the outwardly facing wall, and at least one opening extending from the cavity through the inwardly facing wall.

16. The tool of claim 15, wherein the hook portion further comprises at least one opening extending from the interior cavity through the edge wall.

17. The tool of claim 1, wherein the hook portion comprises a plurality of openings extending through the outwardly facing wall and a plurality of openings extending through the inwardly facing wall, and wherein the pluralities of openings are arranged in at least two rows extending substantially parallel to the second axis.

18. The tool of claim 1, further comprising a fluid bottle and a tube extending therefrom, wherein the tube is connected to a fluid channel extending through the handle portion and the hook portion to the interior cavity.

19. The tool of claim 18, wherein fluid expelled from the fluid bottle passes through the tube and the fluid channel to the interior cavity of the hook portion.

20. The tool of claim 19, further comprising a valve in fluid communication with the bottle and the tube for controlling distribution of the fluid from the fluid bottle.

21. An eyelid retractor, comprising:
a handle portion defining a longitudinal first axis configured to be grasped by a user;
a hook portion for retracting an eyelid connected to the handle portion, the hook portion comprising: inwardly and outwardly facing walls, which are curved about a second axis, which is distinct from the first axis; an edge wall extending between the inwardly and outwardly facing walls; and an interior cavity defined between the walls; and
at least one opening extending through the inwardly facing wall and the at least one opening extending through the outwardly facing wall fluidly connected to the interior cavity and positioned such that fluid in the interior cavity passes through the at least one opening to contact portions of the eye including the eyelid to irrigate the inner surface of the eyelid and to provide liquid towards the bulbar conjunctiva and/or cornea of the eyeball;
wherein the at least one opening is distanced from and distinct from the edge wall.

22. The eyelid retractor of claim 21, wherein the fluid is one from the group of cleaning agents, antiseptics, dyes, and therapeutic agents.

* * * * *